United States Patent [19]

Langecker et al.

[11] 4,310,500
[45] Jan. 12, 1982

[54] METHOD FOR REMOVING VOLATILE AROMATIC COMPOUNDS

[75] Inventors: Gerhard Langecker, Cologne; Hans-Jurgen Gebauer, Troisdorf; Heinrich Hermann, Cologne, all of Fed. Rep. of Germany

[73] Assignee: Josef Meissner GmbH & Co., Cologne, Fed. Rep. of Germany

[21] Appl. No.: 145,637

[22] Filed: May 1, 1980

[30] Foreign Application Priority Data

May 26, 1979 [DE] Fed. Rep. of Germany ....... 2921487

[51] Int. Cl.³ .............................................. C07C 79/10
[52] U.S. Cl. .................................... 423/345; 260/688; 568/927; 568/932; 568/937; 568/939
[58] Field of Search ........................ 423/245; 260/688; 568/932, 934, 939, 940

[56] References Cited

U.S. PATENT DOCUMENTS

| 252,473 | 1/1882 | Kendall | 568/932 |
| 1,380,185 | 5/1921 | Brewster | 260/688 |
| 3,204,000 | 8/1965 | Samuelson | 568/940 X |

*Primary Examiner*—G. O. Peters
*Attorney, Agent, or Firm*—Sprung, Felfe, Horn, Lynch & Kramer

[57] ABSTRACT

In the nitration of a volatile aromatic compound wherein the compound is reacted with a liquid nitrating agent thereby to effect nitration and to produce a waste gas containing some of the aromatic compound, nitrogen oxides and nitric acid, the improvement which comprises contacting the waste gas with fresh nitrating agent thereby to remove the aromatic compound from the gas into the nitrating agent, and thereafter using such nitrating agent to effect subsequent nitration.

4 Claims, 1 Drawing Figure

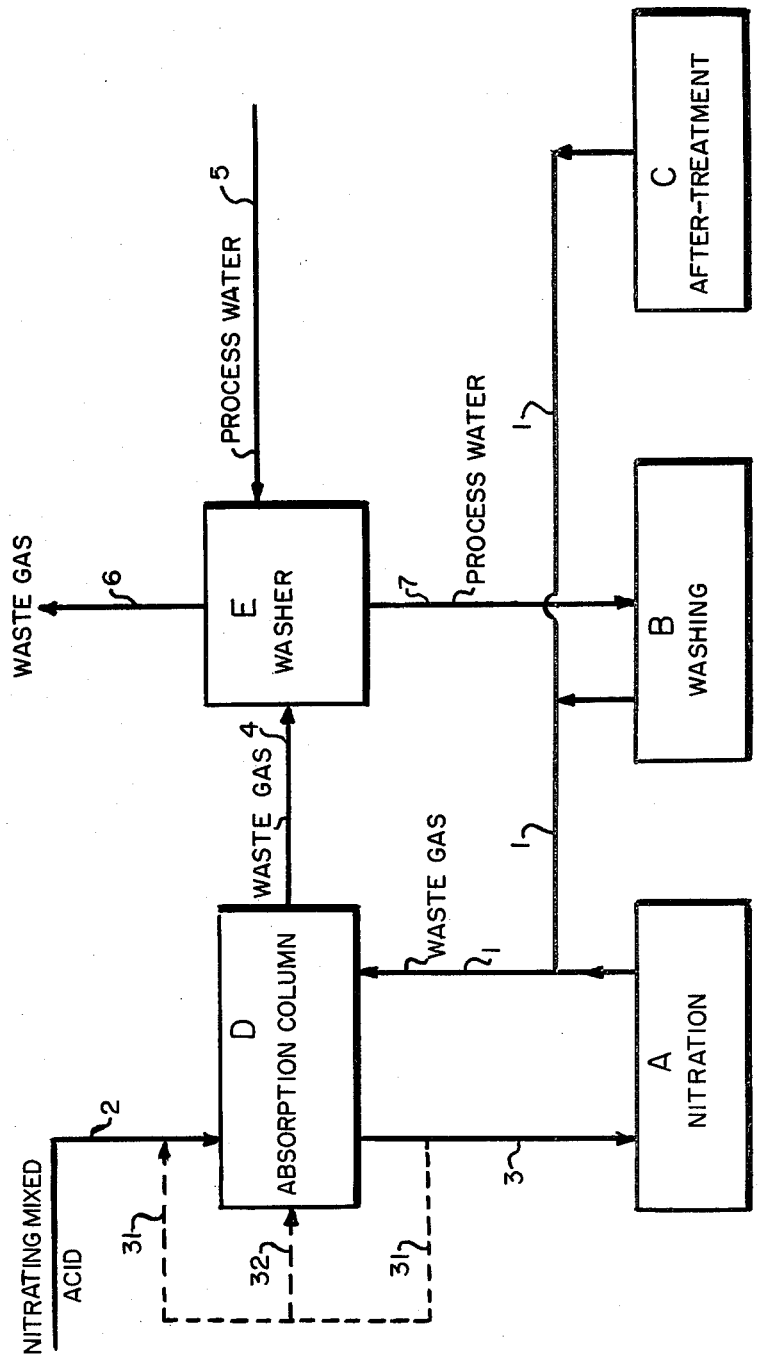

METHOD FOR REMOVING VOLATILE AROMATIC COMPOUNDS

The present invention relates to a method for removing volatile aromatic compounds from waste gases also containing nitrogen oxides and nitric acid.

The removal of volatile aromatic compounds from waste gases is a necessary measure since such substances constitute hazards for humans and the environment, especially health hazards. Various methods are used for the removal of volatile aromatic compounds from waste gases as follows:

Like many other substances, volatile aromatic compounds can be adsorbed on active carbon, which can be regenerated after adsorption of the aromatic compounds. Aromatic compounds from gases have likewise been adsorbed in heavy oil, the aromatic compounds thereafter being separated from the heavy oil by distillation.

In another method, the waste gas containing the aromatic compounds together with other impurities is thermally treated and/or burned in a muffle furnace. This process, however, requires high investment costs and high energy expenditures.

A special problem is encountered in the removal of volatile aromatic compounds from waste gases from plants for nitrating aromatic compounds, in which the aromatics are generally present at high vapor pressures side by side with nitrogen oxides and nitric acid.

It was there found that an adsorption on active carbon could not be carried out economically, since the spent active carbon is not capable of being regenerated because of the also adsorbed nitrogen oxides. Direct burning of the active carbon would require a large expenditure for apparatus as well as high operating costs. Moreover, explosion hazards of active carbon laden with nitrogen oxides prohibit the use of this method in cleaning of waste gases in plants for nitration of aromatic compounds.

An absorption of waste gases into heavy oils, a method which is energy-intensive per se, cannot be employed without considerable additional expenditure because of resinification of the wash oils due to the nitrous gases and nitric acid present in the waste gases.

It is the object of the present invention, therefore, to provide a simple method for removing volatile aromatic compounds from waste gases, which method can also be employed where the waste gases contain additionally nitrogen oxides and nitric acid.

This object is achieved by a method for removing volatile aromatic compounds from waste gases optionally also containing nitrogen oxides and nitric acid which is characterized in that the waste gases are treated with a liquid nitrating compound. Suitable nitrating compounds are all substances that allow a conversion of the aromatic compounds to nitro aromatics or other substances at a lower vapor pressure than that of the aromatic compounds to be absorbed. Examples of such nitrating compounds are:

nitrating nitrogen oxides such as $N_2O_5$, $N_2O_4$, $N_2O_3$,
acyl nitrates, preferably lower acyl nitrates with 1 to 3 carbon atoms, such as cetyl nitrate,
alkyl nitrates, preferably lower alkyl nitrates with 1 to 3 carbon atoms, such as ethyl nitrate,
complex salts of the nitronium ion in appropriate solvent, e.g. nitronium tetrafluoroborate or nitryl chloride, metal nitrates in proton acid, e.g. potassium nitrate in sulfuric acid or acetic acid and nitric acid or nitric acid or mixtures of nitric acid with other substances, e.g. acids like sulfuric acid, phosphoric acid, perchloric acid and mixtures thereof, or acid anhydrides, e.g. oleum, polyphosphoric acids and acetoanhydride, possibly in the presence of solvents such as acetic acid, aliphatic chlorohydrocarbons, and also benzine fractions, nitromethane and other solvents that are inert under the existing conditions, and also adjuvants combined with carrier material or without carrier material that increase the reaction speeds of the nitric acid with the aromatics to be removed beyond that of nitric acid alone, e.g. sulfonic acids, ion exchange resins carrying sulfonic groups or acidic inorganic catalysts of the silicon/aluminum type, such as the zeolites.

Preferred are mixtures of nitric acid with other acids such as sulfuric acid, phosphoric acid, perchloric acid and mixtures thereof and/or acid anhydrides such as oleum, or mixtures of sulfuric acid and polyphosphoric acids, possibly in the presence of solvents like dichloromethane, chloroform, tetrachloromethane and other polychloroethanes. Especially preferred are mixtures of sulfuric acid with contents of 5 to 35 wt.% nitric acid and 50 to 85 wt.% sulfuric acid.

Volatile aromatics that can be removed from waste gases in accordance with the invention are all aromatics that have a noticeable vapor pressure at operating temperature. Examples are:

Benzene and benzene homologues, such as toluene, xylenes, ethylbenzene and other mono- or polynuclear aromatics containing aliphatic side chains which carry in and on the nucleus or the side chain halogen atoms, oxygen, nitrogen, sulfur or other heteroatoms or oxygen- or nitrogen-containing radicals such as hydroxide, ether, ester carbonyl or amino and nitro groups, and likewise sulfur-containing or other heteroatom-containing radicals. Such substances are, for example, singly or multiply halogensubstituted fluorobenzenes and mixedly substituted aromatics, halogenated benzene homologues such as benzotrifluoride, benzotrichloride, benzal chloride, benzyl chloride, chlorobenzotrifluorides, naphthalene or naphthalene derivatives, phenols and phenol ethers such as anisole, aniline and nitrogen-substituted anilines, such as methyl aniline and dimethyl aniline or nitrobenzene and nuclear-substituted nitrobenzenes, such as nitrotoluenes, nitrochlorobenzenes and other nitrobenzenes carrying substituted and unsubstituted side chains, such as nitroethyl benzene and nitrobenzyl halides.

The new method can be carried out in all installations that are suited for the treatment of the waste gases with the nitrating compounds, e.g. absorption plants as used for the treatment of gases for the purpose of removing various components therefrom. Such absorption plants are, for example, one- or multistage absorption columns with appropriate installations, agitator vessel cascades with gassing stirrers, falling film absorbers, spray washers, blow columns, jet and venturi washers.

The optimal operating conditions are required for a complete removal of aromatics contained in waste gases in the absorption plant, such as composition of the nitrating compounds, temperature, pressure, period of contact, etc., will depend on the particular aromatic compound to be removed and must be conformed to the type of aromatic to be removed to achieve the object according to the invention. As an example, in the removal of benzene from the waste gases of benzene nitration the following approximate conditions (weight percent) have proved to be suitable for the purpose:
Composition of nitrating compounds:
  Sulfuric acid 52–60%, nitric acid 22–35%, water 13–18%.
  Reaction temperature 35°–45° C.

In the removal of toluene and/or chlorobenzene from the waste gases of toluene and/or chlorobenzene nitration the following conditions are found to be suitable:
For toluene:
  Composition of nitrating compounds:
    Sulfuric acid 52–60%, nitric acid 18–35%, water 13–22%.
  Reaction temperature 25°–35° C.
For chlorobenzene:
  Composition of nitrating compounds:
    Sulfuric acid 56–62%, nitric acid 25–30%, water 13–14%.
  Temperature of reaction 40°–45° C.

The method according to the invention provides that the collected waste gas coming, for example, from a nitrating plant is passed into an absorption section. In this absorption section, the waste gases are brought in contact with the nitrating compound, possibly in the presence of solvents. The nitrating compounds can preferably be introduced into the absorption section after they have been cooled down. Preferably, so much nitrating compound is added as was originally required for the reaction of the aromatics in the nitrating stage of the manufacturing process. In the absorption section, the aromatic substance contained in the waste gas according to its vapor pressure is converted to nitrated aromatics by means of the nitrating compound.

Depending on the kind of aromatics to be removed from the waste gas, it may be to advantage in this general procedure to increase the amount of nitrating compound that is in contact with the waste gas in the absorption section by returning a portion of the nitrating compound flowing out of the absorption section to its original feeding point or directly back into the absorption section.

The presence of acid gases, such as nitrogen oxides and/or nitric acid, etc., has no adverse effect on the method according to the invention. On the contrary, these gases in accordance with their distribution equilibriums are absorbed along with the aromatic compounds and can even contribute to an improvement of the procedure according to the invention.

Of particular advantage is the method according to the invention in connection with an installation for the nitration of aromatic compounds where the combined spent air from the various stages of the nitrating plant contains, besides the aromatics to be nitrated, nitric acid and nitrogen oxides. A mixture of acids is used therefor that has the same composition as that required for the conversion of the aromatic compounds in the nitrating stage. This washing acid can be introduced directly into the normal nitrating process after leaving the absorption section.

Depending on the amount and type of aromatic compound to be removed from the waste gas, it can be to advantage in this general procedure to vary the quantity of nitrating compound that is in contact with the waste gas in the absorption section so that a portion of the nitrating compound flowing out of the absorption section is returned to its original feeding point or immediately back into the absorption section.

The new method is not limited to a continuous process; it can analogously be implemented in a batch process. The accompanying drawing is a flow sheet of the process in accordance with the invention.

The combined spent air from the various stages of the nitration plant, such as nitration (A), washing (B) and drying (C), is introduced via a line 1 into an absorption column (D) from below.

At the same time, mixed acid as suitable for the nitration is introduced via line 2 at the top of column (D). The nitrating acid existing at the bottom of (D) can either be introduced via line 31 back at the top of the column or via line 32 at some other point into the absorption column or flows directly, via line 3, into the nitrating stage (A).

The waste gas exiting at the top of the column after having been freed from aromatics is introduced, via a line 4, into a washing unit (E), where it is washed with water entering through line 5.

The so treated waste gas leaves the installation via line 6. The process water used for the wash in (E) is likewise used in the nitration, viz. in the washing stage for the washing of the nitrated aromatics, via a line 7.

EXAMPLE 1

50 l/h of spent air saturated with benzene vapor at about 20° C.—corresponding to a benzene content of about 1000,000 ppm—are brought in contact, in counterflow in a column of 50 mm diameter and 1000 mm height filled with raschig rings of a size of 12×8 mm, with 13.7 l/h of a mixed acid of a composition of 53.4% sulfuric acid, 33.4% nitric acid and 13% water at 40° C. The air exiting from the column contains less than 3 ppm in benzene.

EXAMPLE 2

50 l/h of spent air saturated with benzene vapor at about 20° C.—corresponding to a benzene content of about 100,000 ppm—are brought in contact, in counterflow in a column of a diameter of 50 mm and a height of 1000 mm filled with raschig rings of a size of 12×8 mm, with 13.7 l/h of a mixed acid of a composition of 59.2% sulfuric acid, 22.9% nitric acid and 16.9% water at 40° C. The air exiting from the column contains less than 3 ppm in benzene.

The same results are obtained when three times the quantity in waste gas is treated.

It will be appreciated that the instant specification and examples are set forth by way of illustration and not limitation, and that various modifications and changes may be made without departing from the spirit and scope of the present invention.

What is claimed is:

1. In the nitration of a volatile aromatic compound wherein (a) the compound is reacted with an aqueous nitrating agent comprising sulfuric acid and nitric acid thereby to effect nitration and to produce a waste gas containing some of the aromatic compound, nitrogen oxides and nitric acid, the improvement which comprises (b) contacting the waste gas in a gas absorber with fresh nitrating agent thereby to remove the aromatic compound from the gas into the nitrating agent, and thereafter passing such nitrating agent to (a) to effect nitration of fresh feed.

2. The method according to claim 1, wherein the aromatic compound is benzene, the nitrating agent comprises 52–60% sulfuric acid, 22–35% nitric acid and 13–18% water, the temperature in the gas absorber is 35°–45° C. and the benzene content of the gas leaving the absorber is less than 3 ppm.

3. The method according to claim 1, wherein the aromatic compound is toluene, the nitrating agent comprises 52–60% sulfuric acid, 18–35% nitric acid and 13–22% water, the temperature in the gas absorber is 25°–35° C. and the toluene content of the gas leaving the absorber is less than 3 ppm.

4. The method according to claim 1, wherein the aromatic compound is chlorobenzene, the nitrating agent comprises 56–62% sulfuric acid, 25–30% nitric acid and 13–14% water, the temperature in the gas absorber is 40°–45° C. and the chlorobenzene content of the gas leaving the absorber is less than 3 ppm.

* * * * *